(12) United States Patent
Hong et al.

(10) Patent No.: US 8,888,282 B2
(45) Date of Patent: Nov. 18, 2014

(54) ELECTRONIC VISION-THERAPY APPARATUS

(71) Applicant: National Taiwan Normal University, Taipei (TW)

(72) Inventors: Jon-Chao Hong, Taipei (TW); Chao-Hsin Wu, Taipei (TW); Mei-Yung Chen, Taipei (TW)

(73) Assignee: National Taiwan Normal University, Taipei (TW)

( * ) Notice: Subject to any disclaimer, the term of this patent is extended or adjusted under 35 U.S.C. 154(b) by 78 days.

(21) Appl. No.: 13/886,498

(22) Filed: May 3, 2013

(65) Prior Publication Data

US 2013/0342808 A1     Dec. 26, 2013

(30) Foreign Application Priority Data

Jun. 22, 2012   (TW) .............................. 101122457 A

(51) Int. Cl.
| | | |
|---|---|---|
| *A61B 3/00* | (2006.01) | |
| *A61H 5/00* | (2006.01) | |
| *G02C 7/12* | (2006.01) | |
| *G02C 7/02* | (2006.01) | |
| *G02C 7/08* | (2006.01) | |
| *G02C 7/10* | (2006.01) | |

(52) U.S. Cl.
CPC . *G02C 7/021* (2013.01); *A61B 3/00* (2013.01); *A61H 5/00* (2013.01); *G02C 7/083* (2013.01); *G02C 7/101* (2013.01); *G02C 7/105* (2013.01)
USPC ................... 351/203; 351/159.39; 351/159.56

(58) Field of Classification Search
CPC ............ G02B 7/02; G02B 7/022; G02B 7/12; A61B 3/00; A61B 3/0008; A61H 5/00
USPC .............. 351/41, 49, 159.01, 159.39, 159.56, 351/159.6, 159.63, 203; 607/53; 601/37
See application file for complete search history.

(56) References Cited

U.S. PATENT DOCUMENTS

2008/0191965 A1*   8/2008   Pandozy ........................... 345/8

* cited by examiner

*Primary Examiner* — Darryl J Collins
(74) *Attorney, Agent, or Firm* — Krieg DeVault LLP; Brad A. Schepers

(57) ABSTRACT

An electronic vision-therapy apparatus includes a frame, a lens module and a control unit. The lens module includes first and second liquid crystal lenses. The control unit is for controlling the first and second liquid crystal lenses to cooperatively generate and display a light filtering pattern. The light filtering pattern has an opaque part and a plurality of transparent parts. The control unit configures a part of the first liquid crystal lens that corresponds to the opaque part to allow only light having a first polarization to pass therethrough, and configures a part of the second liquid crystal lens that corresponds to the opaque part to allow only light having a second polarization orthogonal to the first polarization to pass therethrough.

14 Claims, 4 Drawing Sheets

ELECTRONIC VISION-THERAPY APPARATUS

CROSS-REFERENCE TO RELATED APPLICATION

This application claims priority of Taiwanese Application No. 101122457, filed on Jun. 22, 2012.

BACKGROUND OF THE INVENTION

1. Field of the Invention

The invention relates to an electronic vision-therapy apparatus, more particularly to an electronic vision-therapy apparatus that is configured to generate a light filtering pattern.

2. Description of the Related Art

A vision-therapy apparatus is designed for assisting a patient with reduced vision (e.g., myopia), by training the patient's extraocular eye muscles to contract normally. As disclosed in Taiwanese Utility Model Patent No. 359171, a conventional vision-therapy apparatus includes an eyeglass frame, and a light filtering board that is mounted on the eyeglass frame. The light filtering board is formed with a light filtering pattern that includes two central orifices each being disposed to correspond in position with one of the two eye pupils of the patient, and two radial orifice sets each being distributed in radial outward directions with respect to a respective one of the central orifices. When using the vision-therapy apparatus, the eye pupils of the patient receive specifically filtered light, and the patient's extraocular eye muscles can be trained accordingly.

Nonetheless, the light filtering pattern must be tailored for each patient with a distinct condition of vision (e.g., myopia with a particular degree). For example, a diameter of each of the two central orifices must be set according to the distinct condition of a respective one of the eyes of the patient. As such, a large number of individual light filtering boards must be manufactured, and a corresponding one of the light filtering boards must be mounted on the eyeglass frame each time a different patient is to use the vision-therapy apparatus. Furthermore, since each of the central orifices must correspond in position with a respective one of the eye pupils, the eyeglass frame is required to be operable to adjust a distance between the central orifices for accommodating various spacings between pupils of different patients.

SUMMARY OF THE INVENTION

Therefore, the object of the present invention is to provide an electronic vision-therapy apparatus configured to display a light filtering pattern that is generated electronically and that can be changed using electrical signals.

Accordingly, an electronicvision-therapy apparatus of the present invention comprises a frame, a lens module and a control unit.

The lens module is mounted on the frame, and includes first and second liquid crystal lenses that are disposed one behind the other.

The control unit is coupled to the lens module for controlling the first and second liquid crystal lenses to cooperatively generate and display a light filtering pattern having an opaque part and a plurality of transparent parts.

Preferably, the control unit configures a part of the first liquid crystal lens that corresponds to the opaque part of the light filtering pattern to allow only light having a first polarization to pass therethrough, and configures a part of the second liquid crystal lens that corresponds to the opaque part of the light filtering pattern to allow only light having a second polarization to pass therethrough. The second polarization is orthogonal to the first polarization.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
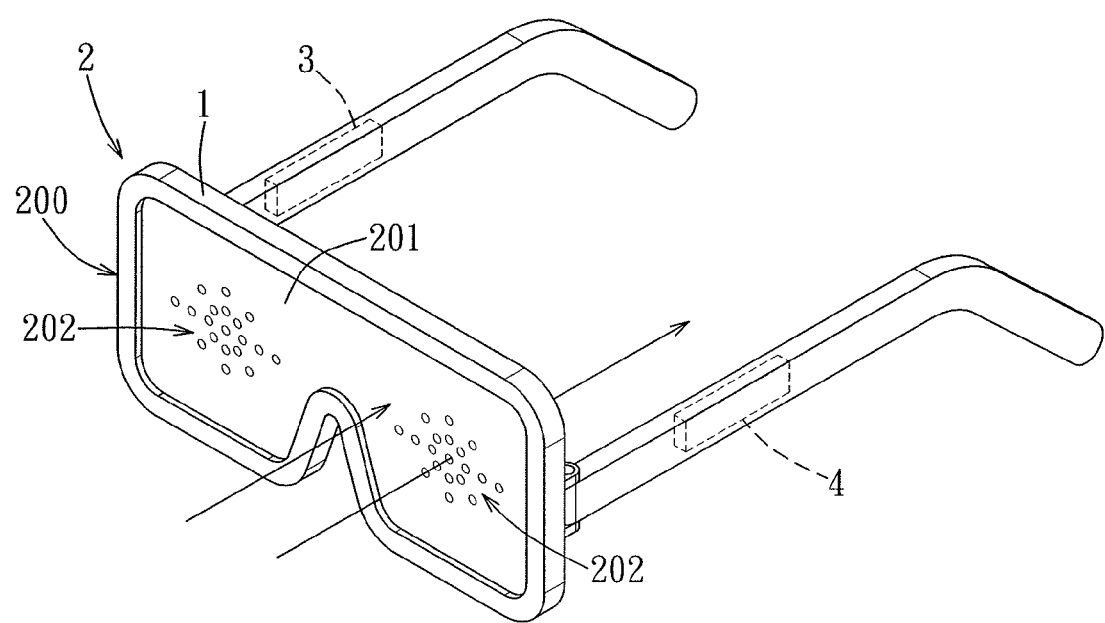
FIG. 1 is a perspective view of a first preferred embodiment of an electronic vision-therapy apparatus according to the invention.

Before the present invention is described in greater detail, it should be noted that like elements are denoted by the same reference numerals throughout the disclosure.

Figure 2:
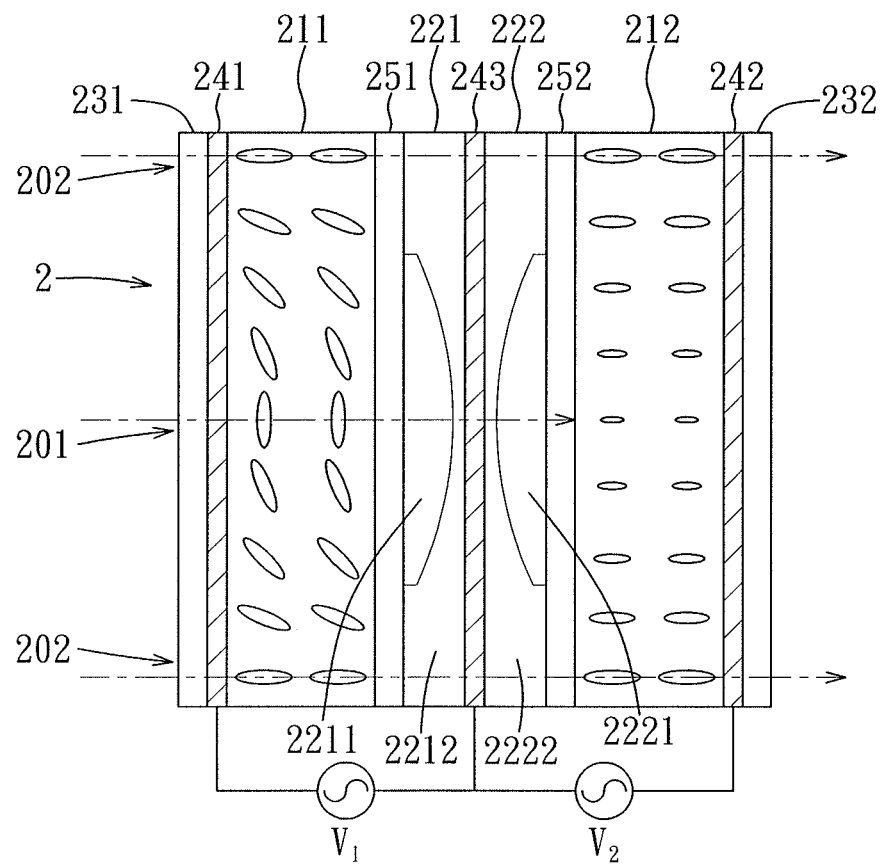
FIG. 2 is a schematic diagram of a lens module of the first preferred embodiment, illustrating light being blocked by an opaque part of a light filtering pattern generated by the lens module.

FIGS. 1 and 2 illustrate the first preferred embodiment of an electronic vision-therapy apparatus according to the present invention. The electronic vision-therapy apparatus comprises a frame 1, a lens module 2, a control unit 3 and a power unit 4. In this embodiment, the frame 1 is an eyeglass frame. The power unit 4 is disposed in the frame 1 for providing power to the control unit 3, and may be a battery set in this particular embodiment.

The lens module 2 is mounted on the frame 1, and includes first and second liquid crystal lenses 211 and 212 that are disposed one behind the other. The control unit 3 is disposed at the frame 1 and is coupled to the lens module 2 for controlling the first and second liquid crystal lenses 211 and 212 to cooperatively generate and display a light filtering pattern 200. The light filtering pattern 200 has an opaque part 201 and a plurality of transparent parts 202.

The lens module 2 in this embodiment further includes: first and second gradient index (GRIN) lenses 221 and 222; first and second transparent substrates 231 and 232; first, second and third transparent electrodes 241 to 243; and first and second alignment layers 251 and 252.

The first GRIN lens 221 is disposed between the first and second liquid crystal lenses 211 and 212, and the second GRIN lens 222 is disposed between the first GRIN lens 221 and the second liquid crystal lens 212. Each of the first and second GRIN lenses 221 and 222 has a first refracting part 2211, 2221 and a second refracting part 2212, 2222. The first refracting parts 2211, 2221 have a refractive index different from that of the second refracting parts 2212, 2222. As a result, the first and second GRIN lenses 221 and 222 are configured to change direction of light passing through the transparent parts 202 of the light filtering pattern 200.

Each of the first and second transparent electrodes 241 and 242 is disposed to cover an outer surface of a respective one of the first and second liquid crystal lenses 211 and 212. The third transparent electrode 243 is disposed between the first and second GRIN lenses 221 and 222, is coupled to the control unit 3, and serves as a common ground.

The first alignment layer 251 interconnects the first liquid crystal lens 211 and the first GRIN lens 221. The second alignment layer 252 interconnects the second liquid crystal lens 212 and the second GRIN lens 222.

Each of the first and second transparent substrates 231 and 232 is disposed to cover a respective one of the first and second transparent electrodes 241 and 242.

The control unit 3 is configured to generate first and second electrical signals $V_1$ and $V_2$, which are provided respectively to the first and second transparent electrodes 241 and 242 for controlling polarization characteristics of the first and second liquid crystal lenses 211 and 212.

Specifically, the first and second electrical signals $V_1$ and $V_2$ transmitted from the control unit 3 control a part of the first liquid crystal lens 211 that corresponds to the opaque part 201 of the light filtering pattern 200 to allow only light having a first polarization to pass therethrough. Similarly, the first and second electrical signals $V_1$ and $V_2$ control a part of the second liquid crystal lens 212 that corresponds to the opaque part 201 of the light filtering pattern 200 to allow only light having a second polarization to pass therethrough. In this embodiment, the second polarization is orthogonal to the first polarization. As such, light is not allowed to pass through the opaque part 201 of the light filtering pattern 200, as shown by an arrow in FIG. 2.

Figure 3:
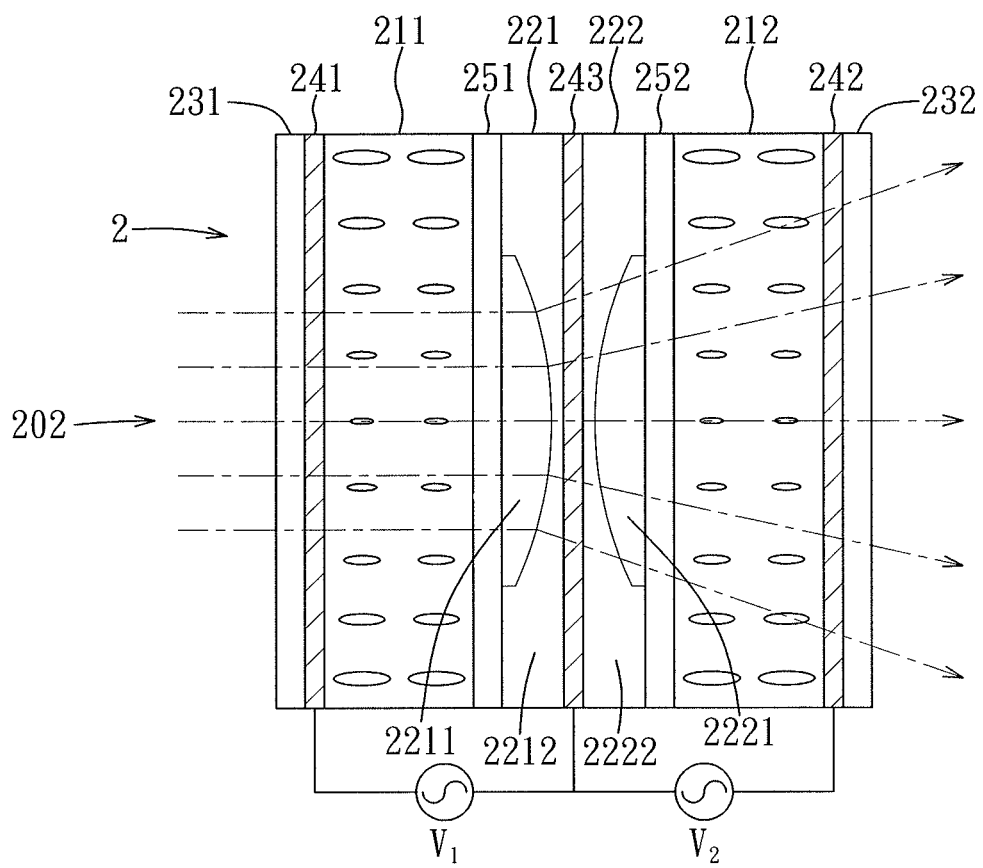
FIG. 3 is another schematic diagram of the lens module, illustrating light being allowed to pass through a transparent part of the light filtering pattern.

To generate the transparent parts 202 of the light filtering pattern 200, for example, the first and second control signals $V_1$ and $V_2$ may configure parts of the first and second liquid crystal lens 211 and 212 that correspond to the transparent parts 202 to allow light having third and fourth polarizations to pass through, respectively (see FIG. 3). The third and fourth polarizations are not orthogonal to each other, and an angle formed by the third and fourth polarizations may be adjusted for allowing at least a portion of light to pass through the transparent parts 202 (hence the name "transparent parts"). The light filtering pattern 200 is then generated.

The first and second GRIN lenses 221 and 222 may also be configured, such that a direction of light passing through the transparent parts 202 of the light filtering pattern 200 is changed to achieve one of a light-converging effect and a light-diverging effect behind the lens module 2 (mimicking, respectively, a convex lens and a concave lens). In this embodiment, each of the first refracting parts 2211, 2221 is configured to have a refractive index $n_1$, and each of the second refracting parts 2212, 2222 has a refractive index $n_2$ that is larger than $n_1$. As shown by arrows in FIG. 3, the resulting configuration of the transparent parts 202 allows light to pass therethrough, and is able to scatter light that passes through to achieve the light-diverging effect. Such configuration is suitable for further providing a vision correcting effect to a patient diagnosed with myopia by focusing light on that patient's retina. This is typically done by a concave lens for vision correction. In other embodiments, the refractive indices of the first and second refracting parts 2211, 2212, 2221 and 2222 can be otherwise adjusted to achieve various effects to focus light on the retinas of the patient. For example, a light-converging effect may be obtained for providing the vision correcting effect to a patient diagnosed with hyperopia.

In some embodiments, refractive indices of the first and second liquid crystal lenses 211 and 212 may also be adjustable by the control unit 3, such that the direction of light passing through the transparent parts 202 can be further changed.

Figure 4:
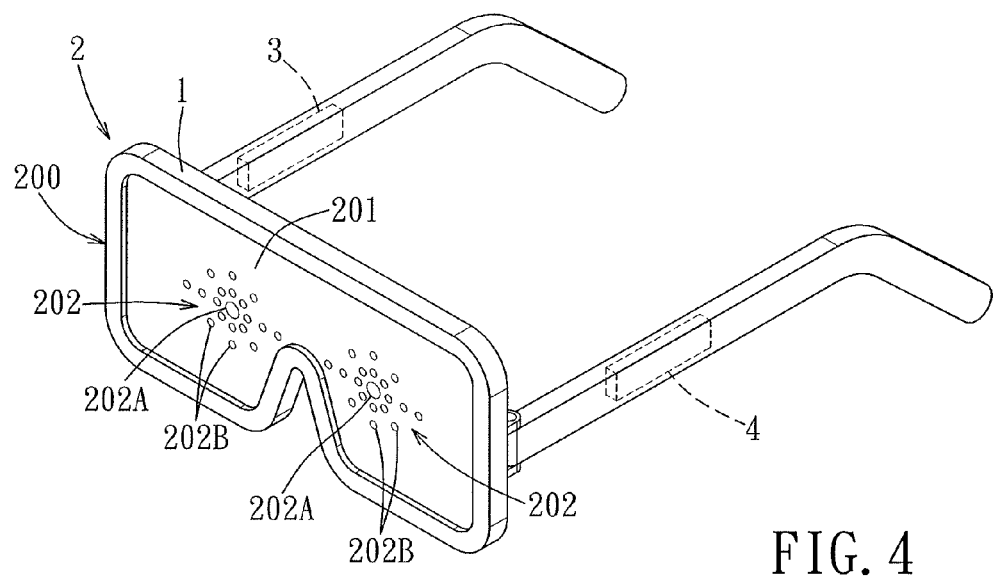
FIG. 4 illustrates an alternative appearance of the light filtering pattern.

As shown in FIG. 4, the transparent parts 202 of the light filtering pattern 200 in this embodiment include a set of central sub-parts 202A that are disposed to correspond in position with an eye pupil, and a set of radial sub-parts 202B that are distributed in radial outward directions with respect to the set of central sub-parts 202A. An appearance of the light filtering pattern 200 may be changed by the control unit 3. For example, the transparent parts 202 can be shifted so that the central sub-parts 202A correspond respectively in position with the eye pupils of the patient. A diameter of the central sub-parts 202A may be adjusted to accommodate different conditions of various patients. For example, the central sub-parts 202A in FIG. 4 have a larger diameter, and are suitable for patients with a lesser degree of myopia.

Figure 5:
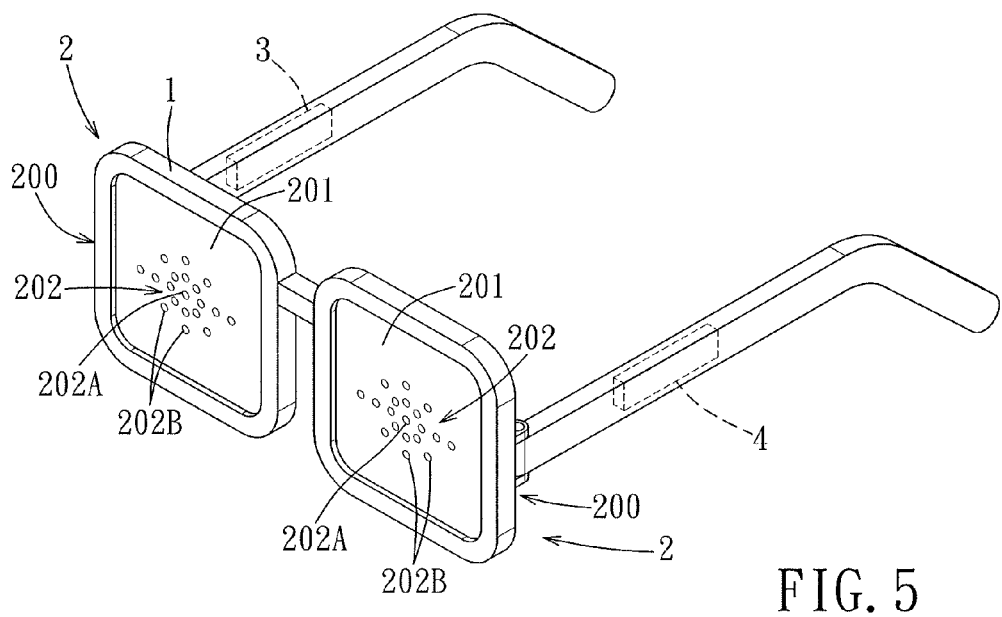
FIG. 5 is a perspective view of a second preferred of the electronic vision-therapy apparatus according to the invention.

FIG. 5 illustrates the second preferred embodiment of the present invention. This embodiment includes an alternatively structured frame 1, and two separate lenses are employed in connection with such a frame 1. Each of the lenses in this embodiment has a structure similar to that of the lens module described in the first preferred embodiment. The second preferred embodiment has the same advantages as those of the first preferred embodiment.

To sum up, the present invention employs the control unit 3 to provide the electrical signals $V_1$ and $V_2$ to the first and second transparent electrodes 241 and 242, so as to control the first and second liquid crystal lenses 211 and 212 to cooperatively generate and display the light filtering pattern 200. As a result, only one, instead of a large number of different lenses, is required to be made for the present invention to accommodate patients with various vision problems. Additionally, each time a new patient uses the electronic vision-therapy apparatus, a new light filtering pattern 200 may be created and displayed on the lens module 2 specifically for that patient using the control unit 3. As such, there is no need to replace the lens module 2 prior to use.

Moreover, it is possible to adjust the refractive index of each of the first and second liquid crystal lenses and first and second GRIN lenses 211, 212, 221 and 222. One of a light-converging effect and a light-diverging effect may be then achieved for correctly focusing light passing through the lens module 2 on the retinas of the patient. Therefore, the electronic vision-therapy apparatus of this invention provides an enhanced therapeutic effect.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An electronic vision-therapy apparatus, comprising:
a frame;
a lens module mounted on said frame, and including first and second liquid crystal lenses that are disposed one behind the other; and
a control unit coupled to said lens module for controlling said first and second liquid crystal lenses to cooperatively generate and display a light filtering pattern having an opaque part and a plurality of transparent parts,
wherein said control unit configures a part of said first liquid crystal lens that corresponds to said opaque part of said light filtering pattern to allow only light having a first polarization to pass therethrough, and configures a part of said second liquid crystal lens that corresponds to said opaque part of said light filtering pattern to allow only light having a second polarization to pass therethrough, the second polarization being orthogonal to the first polarization.

2. The electronic vision-therapy apparatus as claimed in claim 1, wherein said frame is an eyeglass frame.

3. The electronic vision-therapy apparatus as claimed in claim 2, wherein said control unit is disposed at said frame.

4. The electronic vision-therapy apparatus as claimed in claim 1, wherein said control unit is disposed at said frame.

5. The electronic vision-therapy apparatus as claimed in claim 1, wherein said control unit is configured to adjust a refractive index of each of said first and second liquid crystal lenses such that direction of light passing through said transparent parts of said light filtering pattern can be changed.

6. The electronic vision-therapy apparatus as claimed in claim 5, wherein the direction of light passing through said transparent parts of said light filtering pattern is changed to achieve one of a light-converging effect and a light-diverging effect.

7. The electronic vision-therapy apparatus as claimed in claim 1, wherein said lens module further includes a first gradient index (GRIN) lens that is disposed adjacent to at least one of said first and second liquid crystal lenses for changing direction of light passing through said transparent parts of said light filtering pattern.

8. The electronic vision-therapy apparatus as claimed in claim 7, wherein said first GRIN lens is disposed between said first and second liquid crystal lenses.

9. The electronic vision-therapy apparatus as claimed in claim 8, wherein said lens module further includes a second GRIN lens that is disposed between said first GRIN lens and one of said first and second liquid crystal lenses for changing direction of light passing through said transparent parts of said light filtering pattern.

10. The electronic vision-therapy apparatus as claimed in claim 9, wherein:
said lens module further includes first and second transparent electrodes, each disposed to cover an outer surface of a respective one of said first and second liquid crystal lenses; and
said control unit is coupled to said first and second transparent electrodes for providing electrical signals thereto, wherein said first and second liquid crystal lenses are configured to generate and display said light filtering pattern according to the electrical signals provided to said first and second transparent electrodes.

11. The electronic vision-therapy apparatus as claimed in claim 10, wherein said lens module further includes a third transparent electrode disposed between said first and second GRIN lenses and coupled to said control unit.

12. The electronic vision-therapy apparatus as claimed in claim 10, wherein said lens module further includes a first alignment layer that interconnects said first liquid crystal lens and said first GRIN lens, and a second alignment layer that interconnects said second liquid crystal lens and said second GRIN lens.

13. The electronic vision-therapy apparatus as claimed in claim 10, wherein said lens module further includes first and second transparent substrates each disposed to cover a respective one of said first and second transparent electrodes.

14. The electronic vision-therapy apparatus as claimed in claim 1, wherein said transparent parts of said light filtering pattern include a set of central sub-parts that are disposed to correspond in position with an eye pupil, and a set of radial sub-parts that are distributed in radial outward directions with respect to the set of central sub-parts.

* * * * *